United States Patent [19]

Lee

[11] 4,448,966

[45] May 15, 1984

[54] SUBSTITUTED 2-PYRIDYLOXYPHENOXY-ALKANETRIONES

[75] Inventor: Shy-Fuh Lee, Sunnyvale, Calif.

[73] Assignee: Zoecon Corporation, Del.

[21] Appl. No.: 405,852

[22] Filed: Aug. 6, 1982

[51] Int. Cl.³ .................. C07D 213/64; C07D 213/74; A01N 43/40
[52] U.S. Cl. .................................... 546/302; 546/288; 546/296; 546/297; 546/300; 546/157; 546/159; 546/304; 546/307; 546/312; 548/221; 548/222; 548/329; 544/354; 71/94
[58] Field of Search ............... 546/288, 296, 297, 300, 546/302, 304, 307, 312

[56] References Cited

U.S. PATENT DOCUMENTS

| | | | |
|---|---|---|---|
| 4,133,675 | 1/1979 | Schurter et al. | 71/94 |
| 4,216,007 | 8/1980 | Nishiyama et al. | 71/94 |
| 4,348,221 | 9/1982 | Szczepanski et al. | 71/94 |

FOREIGN PATENT DOCUMENTS

| | | | |
|---|---|---|---|
| 4684281 | of 1981 | Japan | 560/62 |
| 8100563 | of 1981 | PCT Int'L Appl. | 71/94 |
| 2040923 | of 1980 | United Kingdom | 546/302 |

*Primary Examiner*—Alan L. Rotman
*Attorney, Agent, or Firm*—Jacqueline S. Larson; Donald W. Erickson

[57] ABSTRACT

Substituted phenoxyalkanetriones and the use thereof for the control of weeds.

6 Claims, No Drawings

SUBSTITUTED 2-PYRIDYLOXYPHENOXY-ALKANETRIONES

This invention relates to certain substituted phenoxyalkanetriones and the use of said compounds for the control of weeds.

More particularly, the compounds of the present invention are represented by the following formula (A):

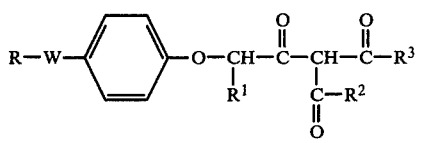

wherein,
R is

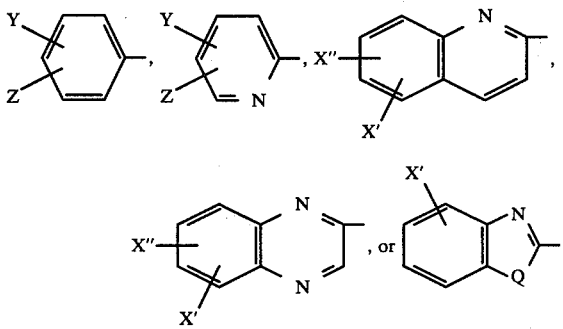

$R^1$ is hydrogen or lower alkyl;
$R^2$ is lower alkyl;
$R^3$ is lower alkyl;
W is oxygen, sulfur or amino;
Q is oxygen, sulfur or amino;
each of Y and Z is independently selected from hydrogen, lower alkyl, lower haloalkyl, lower alkoxy, lower haloalkoxy, halogen, nitro and cyano; and
each of X' and X" is independently selected from hydrogen, lower haloalkyl, lower alkoxy, halogen and nitro, provided that both X' and X" cannot be trifluoromethyl, methoxy or nitro.

In the description and claims hereinafter, each of R—$R^3$, Q, W, X' X" and Y and Z is as defined above, unless otherwise specified.

Compounds of the present invention of formula (A) can be synthesized as outlined below:

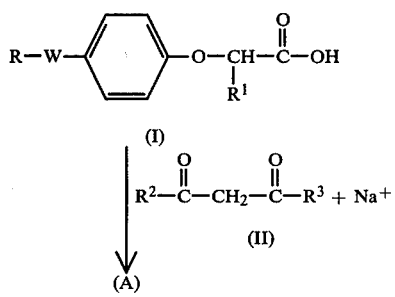

In the above synthesis, a carboxylic acid (I) is converted to its corresponding acid chloride by reaction with oxalyl chloride or thionyl chloride and dimethylformamide (catalytic amount) in an organic solvent such as ether, benzene or tetrahydrofuran (THF), which acid chloride is reacted with the sodium salt of a diketone (II) at reflux temperature and in a solvent such as benzene or THF to yield an alkanetrione of formula (A).

A carboxylic acid of formula (I) may be prepared by the reaction of a phenol (IV) with a 2-halocarboxylate (V; XX is Br or Cl) at room temperature or above in the presence of a base such as alkali metal carbonate or alkali metal hydroxide to give a methyl carboxylate (VI). The carboxylate (VI) is hydrolyzed by reaction with sodium hydroxide followed by hydrochloric acid to give a carboxylic acid (I).

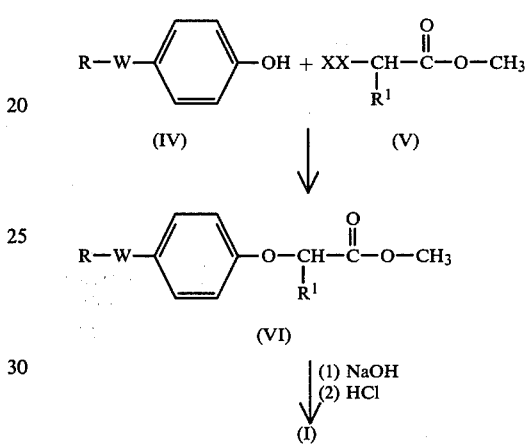

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The compounds of the present invention have one or more asymmetric carbon atoms. The present invention includes each of the optically active isomers and racemic mixtures thereof. In the examples hereinafter, unless otherwise specified, the compound prepared is a racemic mixture.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds. Grass plant (weed) species on which the compounds of the present invention show effective herbicidal activity include shattercane, crabgrass, sprangletop, wild oats, bermudagrass, tall fescue, rice, wheat, barley, corn, blue panicum, foxtails, rough bluegrass, winter rye, annual ryegrass, watergrass and Johnsongrass. It appears to be most effective to apply the active compound prior to the heading stage of the grass weed.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broadspectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

Oxalyl chloride (1.56 g, 1.1 ml, 12.32 mmol) is added to a stirring solution of 2-[4-(4-trifluoromethylphenoxy)phenoxy]propionic acid (2.00 g, 6.16 mmol), dimethylformamide (DMF; 4 drops) and ether (50 ml). The mixture is stirred at RT for 3 hours. Insoluble material is filtered off and solvent is removed in vacuo to give 2-[4-(4-trifluoromethylphenoxy)phenoxy]propionic acid chloride.

A sodium salt solution of 2,4-pentanedione is prepared by dissolving 2,4-pentanedione (10.40 mmol) in benzene (25 ml). Sodium (0.76 g, 7.00 mmol) is added and the mixture is heated under reflux for about 1.5–2 hours.

The above acid chloride, taken up in benzene, is added dropwise to chilled sodium salt of 2,4-pentanedione in benzene, and the mixture is heated under reflux for 2.5 hours. The reaction mixture is washed with water and dried over sodium sulfate, and the benzene is removed by rotoevaporation. The crude product is purified by preparative thin layer chromatography (prep. TLC; silica gel developing with 50% ethyl acetate/hexane) to give 3-acetyl-5-[4-(4-trifluoromethylphenoxy)phenoxy]-2,4-hexanedione (cpd. 1, Table A).

EXAMPLE 2

Following the procedure of Example 1, each of the carboxylic acids under column I is reacted with oxalyl chloride to give the corresponding acid chloride, which is then reacted with the sodium salt of 2,4-pentanedione to give the final 3-acetyl dione in Table A.

I 2. 2-[4-(2-chloro-4-trifluoromethylphenoxy)phenoxy]propionic acid
3. 2-[4-(2,4-dichlorophenoxy)phenoxy]propionic acid
4. 2-[4-(2-nitro-4-trifluoromethylphenoxy)phenoxy]propionic acid
5. 2-[4-(2-methoxy-4-methylphenoxy)phenoxy]propionic acid
6. 2-[4-(2-fluoro-4-trifluoromethylphenoxy)phenoxy]propionic acid
7. 2-[4-(2-chloro-4-trifluoromethylphenylthio)phenoxy]propionic acid
8. 2-[4-(4-trifluoromethylphenylthio)phenoxy]propionic acid
9. 4-(4-trifluoromethylphenoxy)phenoxyacetic acid
10. 4-(2-chloro-4-trifluoromethylphenoxy)phenoxyacetic acid
11. 2-[4-(4-trifluoromethylanilino)phenoxy]propionic acid
12. 2-[4-(2-nitro-4-trifluoromethylanilino)phenoxy]propionic acid
13. 2-[4-(2,4-dichloroanilino)phenoxy]propionic acid
14. 2-[4-(2-bromo-4-chloroanilino)phenoxy]propionic acid
15. 2-[4-(4-chlorophenoxy)phenoxy]propionic acid

EXAMPLE 3

Following the procedure of Example 1, 2-[4-(4-trifluoromethylphenoxy)phenoxy]propionic acid chloride is added to the sodium salt of each of 2,4-hexanedione and 3,5-heptanedione in benzene to give, respectively, 4-acetyl-6-[4-(4-trifluoromethylphenoxy)phenoxy]-3,5-heptanedione (cpd. 16, Table A) and 4-propionyl-6-[4-(4-trifluoromethylphenoxy)phenoxy]-3,5-heptanedione (cpd. 17, Table A).

TABLE A

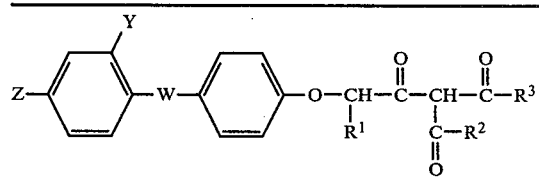

(VII)

| Cpd | Z | Y | W | R¹ | R² | R³ |
|---|---|---|---|---|---|---|
| 1 | CF₃ | H | O | CH₃ | CH₃ | CH₃ |
| 2 | CF₃ | Cl | O | CH₃ | CH₃ | CH₃ |
| 3 | Cl | Cl | O | CH₃ | CH₃ | CH₃ |
| 4 | CF₃ | NO₂ | O | CH₃ | CH₃ | CH₃ |
| 5 | CH₃ | OCH₃ | O | CH₃ | CH₃ | CH₃ |
| 6 | CF₃ | F | O | CH₃ | CH₃ | CH₃ |
| 7 | CF₃ | Cl | S | CH₃ | CH₃ | CH₃ |
| 8 | CF₃ | H | S | CH₃ | CH₃ | CH₃ |
| 9 | CF₃ | H | O | H | CH₃ | CH₃ |
| 10 | CF₃ | Cl | O | H | CH₃ | CH₃ |
| 11 | CF₃ | H | NH | CH₃ | CH₃ | CH₃ |
| 12 | CF₃ | NO₂ | NH | CH₃ | CH₃ | CH₃ |
| 13 | Cl | Cl | NH | CH₃ | CH₃ | CH₃ |
| 14 | Cl | Br | NH | CH₃ | CH₃ | CH₃ |
| 15. | Cl | H | O | CH₃ | CH₃ | CH₃ |
| 16. | CF₃ | H | O | CH₃ | CH₃ | CH₂CH₃ |
| 17. | CF₃ | H | O | CH₃ | CH₂CH₃ | CH₂CH₃ |

EXAMPLE 4

Oxalyl chloride (279 mg, 0.19 ml, 2.2 mmol) is added to a stirring solution of 2-[4-(3-chloro-5-trifluoromethyl-2-pyridyloxy)phenoxy]-propionic acid (400 mg, 1.1 mmol), DMF (1 drop) and ether (15 ml). The mixture is stirred at RT for approximately 3 hours, after which the solvent is removed to give the corresponding acid chloride.

The sodium salt of 2,4-pentanedione is prepared following the procedure in Example 1 by heating together under reflux 2,4-pentanedione (1.8 mmol) and sodium (1.8 mmol), in benzene (20 ml).

The above acid chloride, in benzene, is added to the above sodium salt, chilled, in benzene. The mixture is heated under reflux for 3 hours. The reaction mixture is washed with water and dried over sodium sulfate, and the benzene is removed in vacuo. The crude product is purified by prep. TLC to give 3-acetyl-5-[4-(3-chloro-5-trifluoromethyl-2-pyridyloxy)phenoxy]-2,4-hexanedione (cpd. 18, Table B).

EXAMPLE 5

Following the procedure of Example 4, each of the carboxylic acids under column II is reacted with oxalyl chloride to give the corresponding acid chloride, which is then reacted with the sodium salt of 2,4-pentanedione to give the final 3-acetyl dione in Table B.
19. 2-[4-(5-trifluoromethyl-2-pyridyloxy)phenoxy]propionic acid
20. 2-[4-(3,5-dichloro-2-pyridyloxy)phenoxy]propionic acid
21. 2-[4-(3-fluoro-5-trifluoromethyl-2-pyridyloxy)phenoxy]propionic acid
22. 2-[4-(3-methoxy-5-methyl-2-pyridyloxy)phenoxy]propionic acid
23. 2-[4-(3-nitro-5-trifluoromethyl-2-pyridyloxy)phenoxy]propionic acid
24. 2-[4-(5-trifluoromethyl-2-pyridylthio)phenoxy]propionic acid
25. 2-[4-(3-chloro-5-trifluoromethyl-2-pyridylthio)phenoxy]propionic acid
26. 4-(3-chloro-5-trifluoromethyl-2-pyridyloxy)phenoxyacetic acid
27. 4-(5-trifluoromethyl-2-pyridyloxy)phenoxyacetic acid
28. 2-[4-(3-bromo-5-chloro-2-pyridyloxy)phenoxy]propionic acid

EXAMPLE 6

Following the procedure of Example 4, 2-[4-(3-chloro-5-trifluoromethyl-2-pyridyloxy)phenoxy]propionic acid chloride is added to the sodium salt of each of 2,4-hexanedione and 3,5-heptanedione to give, respectively, 4-acetyl-6-[4-(3-chloro-5-trifluoromethyl-2-pyridyloxy)phenoxy]-3,5-heptanedione (cpd. 29, Table B) and 4-propionyl-6-[4-(3-chloro-5-trifluoromethyl-2-pyridyloxy)phenoxy]-3,5-heptanedione (cpd. 30, Table B).

TABLE B

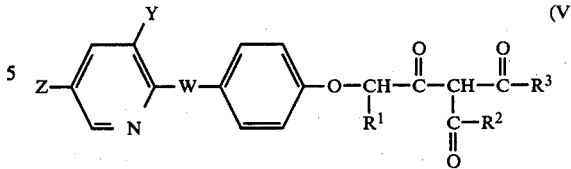

(VIII)

| Cpd | Z | Y | W | R¹ | R² | R³ |
|---|---|---|---|---|---|---|
| 18. | $CF_3$ | Cl | O | $CH_3$ | $CH_3$ | $CH_3$ |
| 19. | $CF_3$ | H | O | $CH_3$ | $CH_3$ | $CH_3$ |
| 20. | Cl | Cl | O | $CH_3$ | $CH_3$ | $CH_3$ |

TABLE B-continued

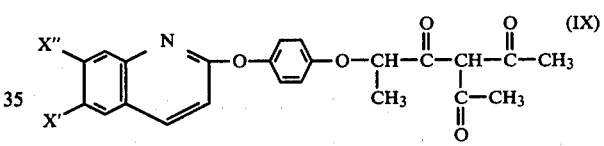

(VIII)

| Cpd | Z | Y | W | R¹ | R² | R³ |
|---|---|---|---|---|---|---|
| 21. | $CF_3$ | F | O | $CH_3$ | $CH_3$ | $CH_3$ |
| 22. | $CH_3$ | $OCH_3$ | O | $CH_3$ | $CH_3$ | $CH_3$ |
| 23. | $CF_3$ | $NO_2$ | O | $CH_3$ | $CH_3$ | $CH_3$ |
| 24. | $CF_3$ | H | S | $CH_3$ | $CH_3$ | $CH_3$ |
| 25. | $CF_3$ | Cl | S | $CH_3$ | $CH_3$ | $CH_3$ |
| 26. | $CF_3$ | Cl | O | H | $CH_3$ | $CH_3$ |
| 27. | $CF_3$ | H | O | H | $CH_3$ | $CH_3$ |
| 28. | Cl | Br | O | $CH_3$ | $CH_3$ | $CH_3$ |
| 29. | $CF_3$ | Cl | O | $CH_3$ | $CH_3$ | $CH_2CH_3$ |
| 30. | $CF_3$ | Cl | O | $CH_3$ | $CH_2CH_3$ | $CH_2CH_3$ |

EXAMPLE 7

Following the procedure of Example 1 or Example 4, oxalyl chloride and 2-[4-(6-fluoro-2-quinolyloxy)phenoxy]propionic acid are reacted together to give the corresponding acid chloride. The acid chloride is then added to the sodium salt of 2,4-pentanedione, giving 3-acetyl-5-[4-(6-fluoro-2-quinolyloxy)phenoxy]-2,4-hexanedione (IX; X' is fluoro and X" is hydrogen).

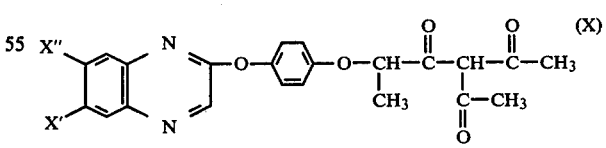

(IX)

In the same manner, 3-acetyl-5-[4-(6,7-dichloro-2-quinolyloxy)phenoxy]-2,4-hexanedione (IX; each of X' and X" is chloro) is prepared from 2-[4-(6,7-dichloro-2-quinolyloxy)phenoxy]propionic acid chloride and the sodium salt of 2,4-pentanedione.

EXAMPLE 8

Following the procedure of Example 1 or Example 4, oxalyl chloride and 2-[4-(6-chloro-2-quinoxalinyloxy)phenoxy]propionic acid are reacted together to give the corresponding acid chloride, which is then reacted with the sodium salt of 2,4-pentanedione to give 3-acetyl-5-[4-(6-chloro-2-quinoxalinyloxy)phenoxy]-2,4-hexanedione (X; X' is chloro and X" is hydrogen).

(X)

In the same manner, each of 2-[4-(6-fluoro-2-quinoxalinyloxy)phenoxy]propionic acid chloride, 2-[4-(6-trifluoromethyl-2-quinoxalinyloxy)phenoxy]propionic acid chloride and 2-[4-(6,7-dichloro-2-quinoxalinyloxy)phenoxy]-propionic acid chloride is reacted with the sodium salt of 2,4-pentanedione to give, respectively,
3-acetyl-5-[4-(6-fluoro-2-quinoxalinyloxy)phenoxy]-2,4-hexanedione (X; X' is fluro and X" is hydrogen);

3-acetyl-5-[4-(6-trifluoromethyl-2-quinoxalinyloxy)-phenoxy]-2,4-hexanedione (X; X' is trifluoromethyl and X" is hydrogen); and 3-acetyl-5-[4-(6,7-dichloro-2-quinoxalinyloxy)-phenoxy]-2,4-hexanedione (X; each of X' and X" is chloro).

EXAMPLE 9

Following the procedure of Example 1 or Example 4, 2-[4-(benzo-1,3-oxazolyl-2-oxy)phenoxy]propionic acid chloride is prepared from oxalyl chloride and the corresponding propionic acid. The acid chloride is then reacted with the sodium salt of 2,4-pentanedione to give 3-acetyl-5-[4-(benzo-1,3-oxazolyl-2-oxy)phenoxy]-2,4-hexanedione (XI; Q is oxygen and X' is hydrogen).

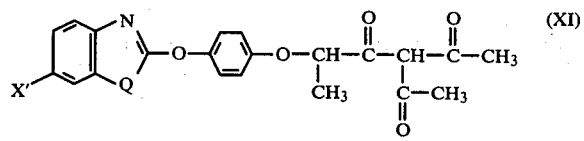

In the same manner, oxalyl chloride and 2-[4-(benzo-1,3-thiazolyl-2-oxy)phenoxy]propionic acid are reacted together to give the corresponding acid chloride, which is then reacted with the sodium salt of 2,4-pentanedione to give 3-acetyl-5-[4-(benzo-1,3-thiazolyl-2-oxy)-phenoxy]-2,4-hexanedione (XI; Q is sulfur and X' is hydrogen).

What is claimed is:

1. A compound of the following formula (A):

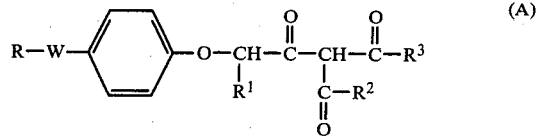

wherein,
R is

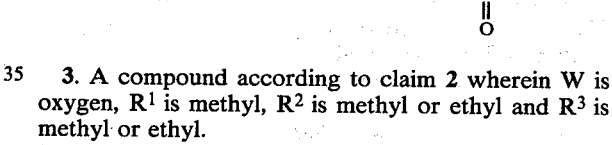

R¹ is hydrogen or lower alkyl;
R² is lower alkyl;
R³ is lower alkyl;
W is oxygen, sulfur or amino; and
each of Y and Z is independently selected from hydrogen, lower alkyl, lower haloalkyl, lower alkoxy, lower haloalkoxy, halogen, and nitro.

2. A compound of the following formula, according to claim 1:

3. A compound according to claim 2 wherein W is oxygen, R¹ is methyl, R² is methyl or ethyl and R³ is methyl or ethyl.

4. A compound according to claim 3 wherein Y is hydrogen or chloro and Z is chloro or trifluoromethyl.

5. The compound 3-acetyl-5-[4-(5-trifluoromethyl-2-pyridyloxy)phenoxy]-2,4-hexanedione, according to claim 4.

6. The compound of 3-acetyl-5-[4-(3-chloro-5-trifluoromethyl-2-pyridyloxy)phenoxy]-2,4-hexanedione, according to claim 4.

* * * * *

UNITED STATES PATENT OFFICE
CERTIFICATE OF CORRECTION

PATENT NO. : 4,448,966
DATED : May 15, 1984
INVENTOR(S) : Shy-Fuh Lee

It is certified that error appears in the above-identified patent and that said Letters Patent are hereby corrected as shown below:

In Claim 1, definition of R, "  "

should read -- 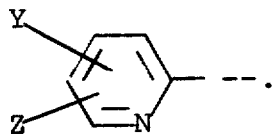 --.

Signed and Sealed this

*Eleventh* Day of *March 1986*

[SEAL]

*Attest:*

DONALD J. QUIGG

*Attesting Officer*     *Commissioner of Patents and Trademarks*